United States Patent
Willems et al.

[11] Patent Number: 5,969,180
[45] Date of Patent: Oct. 19, 1999

[54] METHOD FOR MAKING BIS-XYLENOLS CONTAINING ACID MOIETIES

[75] Inventors: Geert-Jan Willems; Juraj Liska, both of Bergen op Zoom, Netherlands

[73] Assignee: General Electric Company, Pittsfield, Mass.

[21] Appl. No.: 09/016,365

[22] Filed: Jan. 30, 1998

[51] Int. Cl.[6] ............................................. C07C 59/40
[52] U.S. Cl. ................................................ 562/468
[58] Field of Search ............................................. 562/468

[56] References Cited

U.S. PATENT DOCUMENTS

| | | |
|---|---|---|
| 1,193,686 | 6/1970 | Fried et al. . |
| 2,933,520 | 4/1960 | Bader . |
| 3,049,568 | 8/1962 | Apel et al. . |
| 3,049,569 | 8/1962 | Apel et al. . |
| 3,153,001 | 10/1964 | Apel et al. . |
| 3,248,421 | 4/1966 | Smith . |
| 3,567,686 | 3/1971 | White et al. . |
| 3,954,808 | 5/1976 | Elliott et al. . |
| 4,007,282 | 2/1977 | Mauz et al. . |
| 4,375,567 | 5/1983 | Faler . |

FOREIGN PATENT DOCUMENTS

| | | |
|---|---|---|
| 698847 | 12/1964 | Canada . |
| 415200 | of 1991 | European Pat. Off. . |
| 2203594 | of 1972 | Germany . |
| 3329693 | of 1985 | Germany . |
| 61186346 | of 1986 | Japan . |
| 62-70338 | of 1987 | Japan . |

OTHER PUBLICATIONS

Yu et al.: "Acid–Catalyed Condensation of Phenols and Keto Acids" Journal of Organic Chemistry—vol. 23, No. 7, 1958 pp. 1004–1006.

*Primary Examiner*—Paul J. Killos

[57] ABSTRACT

An improved method for the preparation of functionalized substituted bisphenol compound is provided. In particular, there is provided a method of making a functionalized substituted bisphenol compound of the formula:

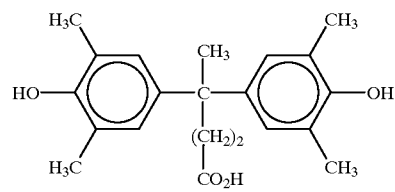

which comprises heating a mixture comprising a 2,6-dimethylphenol and levulinic acid in the presence of an effective amount of a macroreticular ion-exchange resin, optionally with removal of the water of reaction.

10 Claims, No Drawings

METHOD FOR MAKING BIS-XYLENOLS CONTAINING ACID MOIETIES

BACKGROUND OF THE INVENTION

1. Field of the Invention

This invention relates to a process for making functionalized substituted bisphenol compounds using ion exchange resins. More particularly, this invention relates to the preparation of functionalized substituted bisphenol compounds from functionalized ketones or aldehydes with substituted phenols using macroreticular ion exchange resins. In an especially preferred embodiment, this invention relates to the synthesis of an acid functionalized bis-xylenol compound from levulinic acid and 2,6-dimethylphenol using a macroreticular ion exchange resin as catalyst

2. Description of the Prior Art

Condensation reactions, for example, the conversion of various phenols and functionalized ketones into functionalized bis-phenols, have been accomplished with mineral acids. For example, U.S. Pat. No. 3,567,686 describes in general terms the condensation of phenol with keto acids or keto esters such as levulinic acid to prepare bis-phenol compounds of

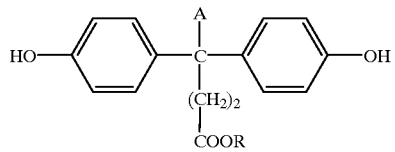

the structure: COOR wherein A is a radical selected from the group consisting of hydrogen, methyl, and phenyl and R is an alkyl group containing one to eighteen carbon atoms, wherein the ester is prepared by reaction of the desired alcohol with the corresponding bis-phenol acid. The esters were described as useful in the polycarbonate resins.

The condensation of mono-alkyl substituted phenols wherein the alkyl group contains at least eight carbon atoms and keto-acids has been described in U.S. Pat. No. 3,954,808. At column 4, beginning at line 37, it is stated that the alkyl-substituted phenol preferably has at least ortho-position unsubstituted on the phenol ring. Acids such as sulphuric acid, p-toluenesulphonic acid, or a mixture of hydrochloric acid and glacial acetic acid were described as catalysts for the condensation reaction. Lactone structures from further condensation of the phenolic hydroxyl groups with the carbonyl-substituted carboxylic acid are also described.

Japanese publication JP62070338 (Tabayashi, et al.) refers to the preparation of functionalized bisphenols from phenols and keto-carboxylic acids using acid catalysis.

Japanese publication JP61186346 (Itsuda, et al.) refers to the preparation of 4,4-bis(4-hydroxyphenyl)pentanoic acid from phenol and levulinic acid using mineral acid catalysis.

Condensation reactions for the production of bis-phenols using ion exchange resins is fairly old and can be found in U.S. Pat. Nos. 3,049,568, 3,049,569 and 3,153,001 (Apel, et al) and 3,221,061 (Grover), among other references. Generally, the bis-phenol described is bis-phenol, a basic building block for polycarbonate resins. The use of ion exchange catalysts for the preparation of bis-xylenols containing acid moieties is unknown.

Due to the costs and efforts associated with the conversion and subsequent purification of bis-xylenols containing acid moieties prepared using mineral acids to catalyze the condensation reactions, it is apparent that a need exists for improved methods for the preparation of these materials.

SUMMARY OF THE PRESENT INVENTION

The long felt needs set forth above have now been satisfied by the important discovery of an improved process for the preparation of bis-xylenols containing acid moieties which comprises heating a mixture comprising substituted phenols and ketones containing acid moieties or aldehydes containing acid moieties in the presence of a macroreticular ion exchange catalyst. These ensuing reactions result in the preparation of the desired bis-xylenols containing acid moieties compounds that are substantially free of non-desired bis-xylenol impurities, in sharp contrast to traditional acid catalyzed condensations used to prepare bis-xylenols containing acid moieties as discussed above. As used herein, "substantially free" means that less than 10% by weight, preferably less than 5% by weight, of non-desired bis-xylenol impurities are produced by the process.

The above mentioned process can be further improved by heating the reaction mixture in the presence of the catalyst with removal of the water of reaction from the reaction mixture. These processes result in the preparation of the desired bis-xylenols containing acid moieties compounds with an increased rate of conversion and improved yields over condensation reactions wherein the water of reaction is not removed.

In a preferred embodiment of the invention, bis-xylenols containing acid moieties can be produced, that is substantially free of impurities, from 2,6-dimethylphenol and 4-oxopentanoic acid.

The functionalized ring substituted bisphenols described in the invention can be used as intermediate compounds or modifiers of various polymeric materials such as functionalization of polyphenylene ether by redistribution reaction, co-monomer for preparation of polycarbonate copolymers, building block to epoxies, intermediate for preparation of FR additives and so forth.

The descriptions which follow provide further details regarding the invention.

DESCRIPTION OF THE DRAWINGS

Not applicable.

DETAILED DESCRIPTION OF THE INVENTION

There is provided a method of making a functionalized substituted bisphenol compound of the formula:

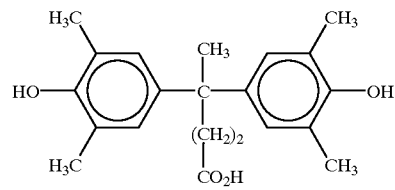

which comprises heating a mixture comprising a 2,6-dimethylphenol and levulinic acid in the presence of a macroreticular ion-exchange resin, optionally with removal of the water of reaction.

There is also provided a method of making a functionalized substituted bisphenol compound of the formula:

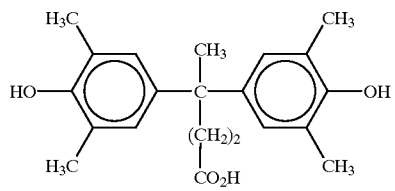

which comprises heating a mixture comprising a 2,6-dimethylphenol and levulinic acid in the presence of a macroreticular ion-exchange resin, optionally with removal of the water of reaction.

There is provided by the present invention a method for the preparation of bis-xylenols containing acid moieties compounds, and in particular bis-(3,5-dimethyl-4-hydroxy-phenyl)pentanoic acid, the method of which comprises heating a mixture of, for example, 2,6-dimethylphenol and 4-ketopentanoic acid in the presence of effective amounts of a macroreticular ion exchange catalyst There is also provided by this invention a method for the preparation of bis-(3,5-dimethyl-4-hydroxy-phenyl) pentanoic acid which comprises heating a mixture of 2,6-dimethylphenol and 4-ketopentanoic acid in the presence of effective amounts of a macroreticular ion exchange catalyst such that the resulting bis-(3,5-dimethyl-4-hydroxy-phenyl) pentanoic acid is substantially free of various reaction impurities.

There is also provided by this invention a method for the preparation of bis-(3,5-dimethyl-4-hydroxy-phenyl) pentanoic acid which comprises heating a mixture of 2,6-dimethylphenol and 4-ketopentanoic acid in the presence of effective amounts of a macroreticular ion exchange catalyst such that the resulting bis-(3,5-dimethyl-4-hydroxy-phenyl) pentanoic acid is substantially free of various reaction impurities, even at low conversions of the 4-ketopentanoic acid.

There is also provided by the present invention a method for the preparation of bis-(3,5-dimethyl-4-hydroxy-phenyl) pentanoic acid which comprises heating a mixture of 2,6-dimethylphenol and 4-ketopentanoic acid in the presence of effective amounts of a macroreticular ion exchange catalyst with the removal of the water of reaction from the reaction mixture.

Various ortho and meta- substituted phenol species of Formula (II):

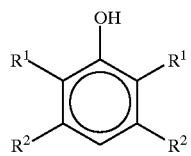

wherein each $R^1$ and $R^2$ is independently hydrogen, halogen, primary or secondary lower alkyl (i.e., alkyl containing up to 7 carbon atoms), phenyl, or alkyl substituted phenyl, could be utilized in the present invention to make various functionalized substituted-bisphenol compounds. Preferably, each $R^2$ independently is hydrogen or primary alkyl. Likewise, the ketones containing acid moieties or aldehydes containing acid moieties of Formula (III):

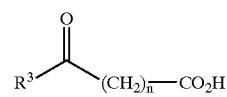

wherein $R^3$ is a hydrogen in the case of aldehydes containing acid moieties or wherein $R^3$ is primary or secondary lower alkyl (i.e., alkyl containing up to about 7 carbon atoms), phenyl, or alkyl substituted phenyl, could also be utilized, and wherein n is on average from one to about twenty. Preferably, $R^3$ is a hydrogen or an alkyl group containing up to about six carbons and n is on average from one to about six. Various combinations are also possible for all the substituents.

The resultant functionalized substituted bisphenol compounds would comprise Formula (IV):

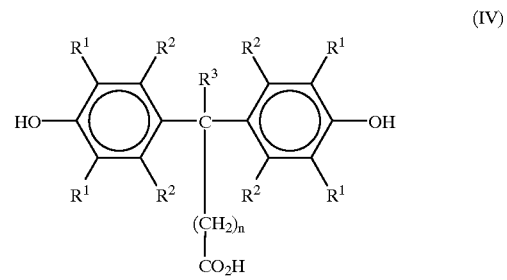

wherein each $R^1$, $R^2$, and $R^3$ are as previously defined. Especially preferred functionalized substituted bisphenol compounds are wherein each $R^1$ is a methyl group, each $R^2$ is a hydrogen, $R^3$ is a lower alkyl moiety of from 1 to about 6 carbons and n is on average from about one to about three. Especially preferred reaction materials are 2,6-dimethylphenol and levulinic acid for the preparation of the corresponding functionalized substituted bisphenol compound wherein each $R^1$ is a methyl group, each $R^2$ is a hydrogen, $R^3$ is a methyl group and n is on average about two.

An illustrative overall reaction scheme for the functionalized substituted bisphenol compound of the present invention can be outlined as follows:

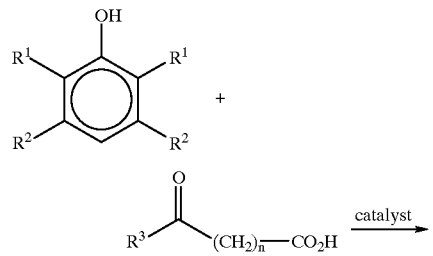

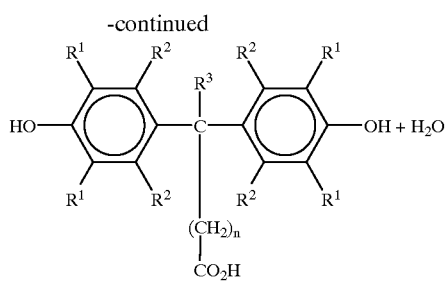

wherein each $R^1$, each $R^2$, and $R^3$ are as previously defined.

The product mixture of the above reaction generally contains functionalized substituted bisphenol compound, excess substituted phenol and the aldehyde and/or ketone starting materials and water (as a reaction by-product), in addition to any inert solvent or water that was added to the reaction mixture. The functionalized substituted bisphenol compound is often isolated via filtration and crystallization techniques known to one skilled in the art. Examples of isolation techniques which can be utilized can be found in U.S. Pat. Nos. 4,400,555 (Mendiratta), 4,507,509 (Mendiratta), and 4,992,598 (Strutz et al), which are incorporated herein by reference.

Any macroreticular ion-exchange resin having appended sulfonic acid groups may be utilized according to the present invention. As taught by Reed, U.S. Pat. No. 4,263,407, the term "macroreticular" as opposed to "microreticular" means porous adsorbance in which the pores are larger than atomic distances and are not part of the polymer structure per se. Rather, the pores are microscopic channels resulting from the squeezing out of an organic precipitant from a copolymer mass. As a consequence, the pore structure is not dependent upon environment and therefore is retained despite contact with various concentrations of electrolyte, solvent and exchangeable ions. The terms macroporous and macroreticular are synonymous, as are the terms microporous and microreticular. Microreticular resins are also called gelular resins.

In microreticular resins (gel-type) the pores are not really pores at all because they are extremely small, usually below 30 A in diameter and will disappear from the polymer structure when the polymer is dry. The microreticular gel resin has a continuous polymer phase while the macroreticular resin is clearly shown to consist of conglomerates of granularly packed macrospheres with both a continuous polymer phase and a continuous void phase. Thus the expression "porous" as used herein refers to channels or openings between conglomerates of minute spherical particles.

Some of the useful macroreticular ion exchange resins are described in U.S. Pat. Nos. 4,375,567 (Faler) and 4,400,555 (Mendiratta), which are incorporated herein by reference. Macroporous resins have been synthesized by the inclusion of various uncross-inked polymers in a monomer mixture. The included polymers are rendered soluble and leachable following sulfonation or amination. The leachable polymers are removed, leaving relatively large-sized pores throughout the cation exchange resin or the anion exchange resin. Other macroporous resins have been synthesized by polymerizing a resin in a solvent which dissolves monomer reagents but exerts essentially no solvent action on the copolymer produced. The polymer matrix of the resin itself may be formed of a variety of materials, such as polystyrene; copolymers of styrene and divinylbenzene; acrylic based polymers; phenolic polymers; and Teflon® type materials such as, for example, tetrafluorocarbon or fluorinated ethylene propylene polymers.

Illustrative sulfonated polystyrene resins which can be utilized in the present invention are formed of copolymers of styrene and divinylbenzene, the latter compound generally being employed as a crosslinking agent at a level of about 1% to about 50% by weight, based on the total resin weight. The degree of crosslinking of the polymer enables higher throughput rates in a continuous reaction process by preventing deformation of the ion exchange resin. In order to provide useful macroreticular ion exchange resins, resin designers have adjusted hydration, swelling, and porosity of ion exchange resins through proper choice of polymers and copolymers and through control of the degree of cross4inking of polymer chains. Additionally, resins having pores with dimensions significantly larger than the molecular distance between adjacent copolymer chains (macroporous resins) have been synthesized. Commercial microreticular ion exchange beads have surface areas less than 0.1 square meters/gram whereas, most macroreticular ion-exchange beads of the same particle size have surface areas in the 5-200 square meters/gram range. Specific examples of commercially available sulfonic acid containing macroreticular ion exchange resins include: resins sold under the tradenames AMBERLITE and AMBERLYST resins, available from Rohm and Haas; DOWEX resins, available from Dow Chemical Company; and LEWATIT BG, available from Bayer.

The resins are generally purified prior to use by means of repeated washing with several volumes of deionized water prior to use. Ion exchange resins that have been treated with repeated washings with base followed with washing with acid as described in U.S. Pat. No. 4,847,432 (Faler), which is incorporated herein by reference, are also useful.

The ion exchange resins can be predried prior to use in the condensation reaction in a standard method such as heating in a dry air stream at elevated temperatures, typically from about 90° C. to about 100° C. The ion exchange resin can also be used in the present invention wet, that is, without a drying step when the water washing step is utilized. When the ion exchange resin is used without a predrying step, the resin can be dehydrated by passing anhydrous solvent, such as anhydrous 2,6-dimethylphenol, phenol, or toluene, through a column containing the wet resin prior to the condensation reaction.

A rate accelerator or co-catalyst may be used in some embodiments of the present invention in order to effectively accelerate the condensation reaction. A useful class of accelerators are mercaptans. The mercaptan can be an alkyl mercaptan and can have other non-alkyl moieties present such as, for example, carboxyl. Sometimes a mixture of mercaptans is used. The mercaptan can be present either as a free promoter in the reaction mixture or can be bound to a polymeric resin such as the ion exchange resin. An effective amount of free mercaptan present as a promoter is typically in the range of about 1:20 to 1:1 mole ratio of mercaptan to ketone, although the exact amount utilized is not critical. The ion exchange resins can be partially modified by reacting the acid groups on the resin with mercapto alkyl amines, by partially esterifying the acid resins with a mercapto alcohol, or with an alkyl amine precursor such as thiazolidines. It is sometimes preferred to use a polymer bound mercaptan as a promoter to avoid having the promoter present in the final reaction mixture. Examples of the preparation of polymer bound mercaptan promoters can be found in U.S. Pat. Nos. 4,294,995 (Faler et al), 4,396,728 (Faler) and 4,584,416 (Pressman et al), all of which are incorporated herein by reference.

The unmodified ion exchange resins generally have an ion exchange capacity of at least 2.0 milliequivalents of $H^+$, with exchange capacities in the range of from about 3 milliequivalents of $H^+$ to about 6 milliequivalents of $H^+$; per gram of dry resin. About 5% to about 35% or more, of the acid sites are modified by reacting the acid sites with a mercapto group, for the case when the mercaptan is bound.

The present process for conducting the condensation reaction of a substituted phenol and ketone or aldehyde containing the acid functionality to form the functionalized substituted bisphenol compounds can be carried out in accordance with methods in the art for ion exchange catalyzed condensation reactions. The condensation reaction can be carried out either in a batch mode or in a continuous process. Mole ratios of substituted phenol to the aldehyde or ketone can range from about 4:1 to about 20:1 or an even greater amount of substituted phenol. Substantially anhydrous reaction conditions can be used whereby the water reaction by-product is maintained at less than 2% through the use of anhydrous feed stocks and anhydrous reaction conditions known in the art. Azeotropic removal of the water of reaction can be readily achieved through the use of a toluene azeotrope. Examples of reaction conditions can be found in U.S. Pat. Nos. 4,375,567 (Faler), 4,391,997 (Mendiratta), and 4,590,303 (Mendiratta), all of which are incorporated herein by reference.

Optimum results are obtained for the condensation reaction when the reaction temperature is maintained between about 50° C. and about 90° C. The reaction can be carried out at atmospheric, sub-atmospheric, or super-atmospheric pressures. In general, the reaction is maintained under an inert and preferably, anhydrous atmosphere in the reaction. In a continuous reaction operation, a slightly elevated pressure is preferred to insure adequate flow of the materials through the reaction system.

Removal of at least a portion, preferably a substantial portion, of the water of reaction is preferred to drive the condensation to near completion. This can be accomplished by several methods including sparging the reaction with an inert dry gas such as, for example, dry nitrogen gas, or azeotropic removal of the water with an inert solvent such as, for example, toluene, methylene chloride, 1,2-dichloroethane, or mixtures of solvents capable of forming azeotropes with water. Molecular sieves may also be used to remove the water of reaction. Organic sponges for water such as, for example, anhydrides and ortho esters typically are not preferred as they can also react with the desired phenolic products, the aldehyde, the ketone, and/or co-catalyst to result in a reduction in the yield obtained. Organic sponges that would be selective for water but not phenolic compounds, the aldehyde, the ketone, and/or the co-catalyst would, however, be useful for the present reaction.

For removal of the water of reaction from the reaction mixture, a sparge of dry inert gas through the reaction solution or ion exchange bed during the reaction is sufficient to remove the water. Various reactor designs are known in the art for both batch and continuous processes for sparging a reactor, collecting the wet effluent by evaporation and distillation followed by returning the dry solvent to the reaction. In a batch reaction mode, the distilled solvent can be recycled into the next batch or added back into the same reaction.

Azeotropic removal of the water of reaction can be achieved in a likewise fashion to sparging the reaction mixture. It is preferable that the azeotropic solvent selected have an azeotropic boiling point lower than the substituted phenol utilized in the condensation reaction in order to prevent unintentional loss of the substituted phenol from the reaction mixture. Substituted phenol can, however, be utilized for the azeotropic removal of the water of the reaction with replacement of the substituted phenol in order to maintain the level of substituted phenol within the preferred range. It is also preferable that the azeotropic solvent not be reactive towards any of the chemical reagents or the desired product. Mixtures of solvents can also be utilized. Reactor designs are known in the art for both batch and continuous processes to recycle the azeotropic solvent either into the same reaction for continuous removal of water or into a subsequent condensation reaction.

The removal of the water can be done continuously during the condensation reaction or can be done in steps at intervals during the reaction. It is also possible to utilize a single water removal step after the reaction has substantially progressed to further the reaction towards completion. By substantially progressed is meant that the percentage conversion of the starting materials into the functionalized substituted bisphenol compounds is at least about 20 mole percent converted.

With respect to the preparation of functionalized substituted bisphenol compounds utilizing a sulfonated aromatic organic polymer containing N-alkylaminoorganomercaptan groups as the ion exchange resin, a mixture of substituted phenol and ketone or aldehyde containing carboxylic acid moieties can be heated in the presence of the macroreticular cation-exchange resin prepared in accordance with the practice of the present invention. There can be utilized 4-20 moles of the phenol per mole of the ketone/aldehyde which can be heated at a temperature in the range of from about 50° C. to about 110° C. with agitation. The ion-exchange resin can be employed at from about 0.1% to about 50% or more by weight, based on the weight of the total mixture in instances where a batch process is used. In a preferred procedure for making functionalized substituted bisphenol compounds in a continuous manner, the ion-exchange resin can be used in a column which can be operated at a temperature of about 50° C. to about 100° C. The mole ratio of reactants can vary widely, such as from about 3 to 1 to about 30 to 1 or more, moles of substituted phenol per mole of ketone/aldehyde. It is preferred, however, to use the reactants at a mole ratio of about 5 to 1 to about 20 to 1 moles of substituted phenol per mole of ketone/aldehyde. The impurities present in the reaction mixture are generally less than 30%, preferably less that 20% and most preferably less than 10%; wherein the % by area of the impurities was determined by liquid chromatography analysis.

One method of recovering the functionalized substituted bisphenol compounds reaction product, for example, bis-(3,5-dimethyl-4-hydroxy-phenyl)pentanoic acid, is by crystallizing the functionalized substituted bisphenol compound reaction product from the reactor effluent. Another procedure involves the partial distillation to remove the substituted phenol followed by recrystallization of the residual functionalized substituted bisphenol compound using methanol, methanol/water, ethanol, ethanol/water, 2-propanol, 2-propanol/water, phenol, phenol/methylene chloride, or phenol/1,2-dichloroethane as the solvent. A crystallization procedure for BPA recovery is also shown in U.S. Pat No. 4,375,567 (Faler), which is incorporated herein by reference, is also useful for recovering functionalized substituted bisphenol compound. If desired, in addition to, or instead of recrystallization, the crude functionalized substituted bisphenol compound reaction product solution or the functionalized substituted bisphenol compound dissolved in a suitable solvent can be treated with activated carbon or a sodium borohydride solution as illustrated by U.S. Pat. No. 4,992,598 (Strutz, et al).

For another embodiment of the present invention, the functionalized substituted bisphenol compound reaction mixture can be admixed with a non-solvent for the functionalized substituted bisphenol compound to cause the functionalized substituted bisphenol compound to precipitate from the reaction solution. It is preferred that the starting materials as well as the reaction impurities be soluble in the non-solvent for the functionalized substituted bisphenol compound. It is also preferred that the non-solvent and the starting materials be readily separable from each other such that the starting materials could be recycled into subsequent functionalized substituted bisphenol compound synthesis reactions. Non-limiting examples for the non-solvent include both halogenated and non-halogenated lower alkyl and aryl solvents. Preferred non-solvents include, for example, 1,2-dichloroethane, dichloromethane, toluene, and xylene. Especially preferred are the lower alkyl halogenated solvents, including 1,2-dichloroethane, dichloromethane.

All patents cited by reference are incorporated by reference herein.

In order that those skilled in the art will be better able to practice the invention, the following examples are given by way of illustration and not by way of limitation.

EXAMPLES

Mineral Acid Catalysis.

A mixture of 50.0 g (409 mmol) of 2,6-xylenol, 1.134 g (9.8 mmol) of levulinic acid, and 2.35 g (26 mmol) of concentrated hydrochloric acid was stirred in a flask while heated to about 80° C. for about 12 hours. The reaction progress was monitored by high pressure liquid chromatography (HPLC) using aliquots diluted into acetonitrile. Very low conversion (<5%) into the desired functionalized substituted bisphenol compound was obtained.

Ion Exchange Catalyst Preparation.

The ion exchange catalyst was prepared as follows:

1. The resin was washed in a Buchner funnel with several volumes of deionized water until the filtrate was colorless. Then, the majority of the water was removed by washing the resin with methanol.

2. The majority of the remaining water was removed by drying the resin in a forced air oven at 95° C. to 100° C. for 24 to 48 hrs. (Some darkening of the resin may occur. Heating in excess of 100° C. can result in resin oxidation.)

3. Before use, the resin was dried overnight at about 90° C. in a vacuum oven.

Microreticular Ion-Exchange Resin Catalysis.

A mixture of 50.0 g (409 mmol) of 2,6-xylenol, 1.134 g (9.8 mmol) of levulinic acid, and 5.0 g of AMBERLYST 31 gellular ion-exchange resin from Rohm & Haas was stirred in a flask while heated to about 80° C. for about 24 hours. The reaction progress was monitored by high pressure liquid chromatography (HPLC) using aliquots diluted into acetonitrile. Very low conversion (<5%) into the desired functionalized substituted bisphenol compound was obtained, even after 24 hours.

Macroreticular Ion-Exchange Resin Catalysis Without Water Removal.

A mixture of 50.0 g (409 mmol) of 2,6-xylenol, 1.134 g (9.8 mmol) of levulinic acid, and 5.0 g of AMBERLYST 36 macroreticular ion-exchange resin from Rohm & Haas was stirred in a flask while heated to about 80° C. for about 15 hours. The reaction progress was monitored by high pressure liquid chromatography PLC) using aliquots diluted into acetonitrile. Conversion of about 85% into the desired functionalized substituted bisphenol compound was obtained.

Macroreticular Ion-Exchange Resin Catalysis With Water Removal.

A mixture of 50.0 g (409 mmol) of 2,6-xylenol, 1.134 g (9.8 mmol) of levulinic acid, and 5.0 g of AMBERLYST 36 macroreticular ion-exchange resin from Rohm & Haas was stirred in a flask while heated to about 95° C. for about 24 hours. Benzene was added and water was continuously removed as an azeotrope using a Dean-Stark trap. The reaction progress was monitored by high pressure liquid chromatography (HPLC) using aliquots diluted into acetonitrile. Conversion of about 89% into the desired functionalized substituted bisphenol compound was obtained.

These results illustrate that high conversion into the desired functionalized substituted bisphenol compounds using ion exchange resins can be achieved with the use of macroreticular ion exchange resins.

What is claimed:

1. A method of making a functionalized substituted bisphenol compound of the formula:

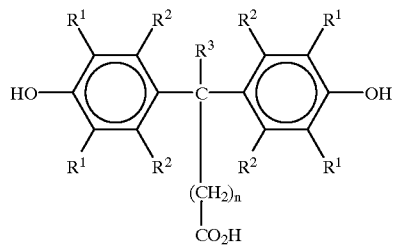

which comprises heating a mixture comprising a phenol species of the formula:

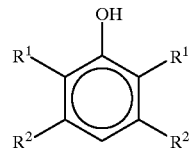

and a carboxylic acid-containing material of the formula:

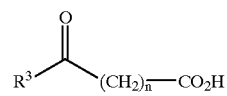

in the presence of a macroreticular ion exchange catalyst, wherein each $R^1$ and $R^2$ is independently hydrogen, halogen, primary or secondary lower alkyl, phenyl, or alkyl substituted phenyl, $R^3$ is a hydrogen, primary or secondary lower alkyl, phenyl, or alkyl substituted phenyl, and n is on average from one to about twenty.

2. The method of claim 1, wherein the macroreticular ion exchange resin is made from a polymer selected from the group consisting of polystyrene, copolymers of styrene and divinylbenzene, acrylic based polymers, phenolic polymers, tetrafluorocarbon and fluorinated ethylene propylene polymers.

3. The method of claim 1, wherein the ion exchange resin contains sulfonic acid groups.

4. The method of claim 1, wherein the water of reaction is removed from the reaction mixture.

5. The method of claim 4, wherein the water of reaction are removed with the aid of sparging the reaction with an inert gas, with an azeotrope, or with both sparging and an azeotrope.

6. The method of claim 1, wherein the phenol species is 2,6-dimethylphenol and the carboxylic acid-containing material is levulinic acid.

7. The method of claim 6, wherein the mole ratio of 2,6-dimethylphenol to levulinic acid is at least 2:1.

8. The method of claim 1, which consists essentially of heating a mixture comprising the phenol species and the carboxylic acid-containing material in the presence of a ion exchange catalyst, optionally with the removal of the water of reaction.

9. The method of claim 8, wherein the ion exchange resin contains sulfonic acid groups.

10. A method of making a functionalized substituted bisphenol compound of the formula:

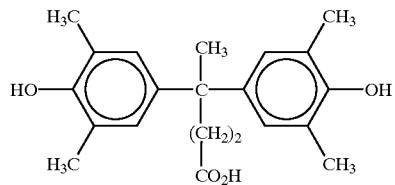

which comprises heating a mixture comprising a 2,6-dimethylphenol and levulinic acid in the presence of a macroreticular ion-exchange resin, optionally with removal of the water of reaction.

* * * * *